US005709876A

United States Patent [19]
Fuisz

[11] Patent Number: 5,709,876
[45] Date of Patent: Jan. 20, 1998

[54] SACCHARIDE-BASED MATRIX

[75] Inventor: Richard C. Fuisz, Great Falls, Va.

[73] Assignee: Fuisz Technologies Ltd., Chantilly, Va.

[21] Appl. No.: 482,778

[22] Filed: Jun. 7, 1995

Related U.S. Application Data

[62] Division of Ser. No. 365,591, Dec. 28, 1994, Pat. No. 5,597,608, which is a division of Ser. No. 847,595, Mar. 5, 1992, Pat. No. 5,387,431, which is a continuation-in-part of Ser. No. 782,430, Oct. 25, 1991, abandoned.

[51] Int. Cl.$^6$ ...................................................... A61K 47/00
[52] U.S. Cl. ........................ 424/439; 424/488; 424/469; 536/103; 536/123.13; 514/778
[58] Field of Search ............................ 424/439, 488; 536/103, 123.13; 514/778

[56] References Cited

U.S. PATENT DOCUMENTS

| | | | |
|---|---|---|---|
| Re. 32,016 | 10/1985 | Esders et al. | 435/28 |
| 796,528 | 8/1905 | Pollock . | |
| 816,055 | 3/1906 | Zoeller . | |
| 847,366 | 3/1907 | Pollock . | |
| 856,424 | 6/1907 | Robinson . | |
| 1,489,342 | 4/1924 | Brent . | |
| 1,541,378 | 6/1925 | Parcell . | |
| 2,918,404 | 12/1959 | Mende et al. | 167/58 |
| 3,019,745 | 2/1962 | Du Bois et al. | 107/8 |
| 3,036,532 | 5/1962 | Bowe | 107/8 |
| 3,067,743 | 12/1962 | Merton et al. | 128/270 |
| 3,070,045 | 12/1962 | Bowe | 107/8 |
| 3,073,262 | 1/1963 | Bowe | 107/8 |
| 3,095,258 | 6/1963 | Scott | 18/54 |
| 3,118,396 | 1/1964 | Brown et al. | 107/8 |
| 3,118,397 | 1/1964 | Brown et al. | 107/8 |
| 3,125,967 | 3/1964 | Bowe | 107/8 |
| 3,131,428 | 5/1964 | Mika | 18/8 |
| 3,308,221 | 3/1967 | Opfell | 264/174 |
| 3,324,061 | 6/1967 | Tanquary et al. | 260/29.2 |
| 3,396,035 | 8/1968 | Kessinger | 99/94 |
| 3,455,838 | 7/1969 | Marotta et al. | 252/316 |
| 3,482,998 | 12/1969 | Carroll et al. | 99/108 |
| 3,523,889 | 8/1970 | Eis | 210/20 |
| 3,557,717 | 1/1971 | Chivers | 107/54 |
| 3,557,718 | 1/1971 | Chivers . | |
| 3,595,675 | 7/1971 | Ash et al. | 99/130 |
| 3,615,671 | 10/1971 | Schoaf | 99/78 |
| 3,625,214 | 12/1971 | Higuchi | 128/260 |
| 3,676,148 | 7/1972 | De Weese et al. | 99/1 |
| 3,686,000 | 8/1972 | Lawrence . | |
| 3,723,134 | 3/1973 | Chivers | 99/134 |
| 3,749,671 | 7/1973 | Gedge et al. | 252/89 |
| 3,762,846 | 10/1973 | Chivers | 425/7 |
| 3,766,165 | 10/1973 | Rennhard | 260/209 |
| 3,856,443 | 12/1974 | Salvi | 425/9 |
| 3,875,300 | 4/1975 | Homm et al. | 424/28 |
| 3,876,794 | 4/1975 | Rennhard | 426/152 |
| 3,907,644 | 9/1975 | Möllering et al. | 195/99 |
| 3,912,588 | 10/1975 | Möllering et al. | 195/29 |
| 3,925,164 | 12/1975 | Beaucamp et al. | 195/103.5 |
| 3,925,525 | 12/1975 | LaNieve | 264/40 |
| 3,930,043 | 12/1975 | Waring et al. | 426/515 |
| 3,951,821 | 4/1976 | Davidson | 252/1 |
| 3,972,725 | 8/1976 | Nicol | 127/58 |

(List continued on next page.)

FOREIGN PATENT DOCUMENTS

| | | |
|---|---|---|
| 609135 | 4/1988 | Australia . |
| 609137 | 4/1988 | Australia . |
| 900605 | 11/1977 | Belgium . |
| 1303511 | 4/1988 | Canada . |
| 0 158 460 A1 | 3/1985 | European Pat. Off. . |
| 0 287 488 A1 | 3/1988 | European Pat. Off. . |
| 0 387 950 a1 | 8/1990 | European Pat. Off. . |
| 86052 | 4/1988 | Israel . |
| 86053 | 4/1988 | Israel . |
| 88/2770 | 4/1988 | South Africa . |
| 88/2771 | 4/1988 | South Africa . |
| 89/9318 | 12/1989 | South Africa . |
| 90/2139 | 3/1990 | South Africa . |
| 90/8406 | 8/1991 | South Africa . |
| 519858 | 5/1971 | Switzerland . |
| 489211 | 7/1986 | Switzerland . |
| 2 155 934 B | 3/1985 | United Kingdom . |
| WO 85/03414 | 1/1985 | WIPO . |
| WO 91/18613 | 5/1991 | WIPO . |

OTHER PUBLICATIONS

R.H. Doremus, "Crystallization of Sucrose From Aqueous Solution, " *Journal of Colloid and Interface Science*, 104 , pp. 114–120 (1985).

P. Bennema., "Surface Diffusion and the Growth of Sucrose Crystals, " *Journal of Crystal Growth*, 3,4 pp. 331–334 (1968).

T.D. Simpson, et al., "Crystalline Forms of Lactose Produced in Acidic Alcoholic Media," *Journal of food Science*, 47, pp. 1948–1954 (1982).

A.D. Randolph, et al., "Continuous Sucrose Nucleation," *The International Sugar Journal*, pp. 8–12 35–38 (1974).

K.B. Domovs, et al., "Methanol–Soluble Complexes of Lactose and of other Carbohydrates," *J. Dairy Science*, 43, pp. 1216–1223 (1960).

A. D. Randolph, et al., "Continuous Sucrose Nucleation, " *The International Sugar Journal*, p. 35–38 (1974).

A.D. Randolph, et al., "Continuous Sucrose Nucleation," *The International Sugar Journal*,pp. 73–77 (1974).

ICI Americas, Inc., "ICI Americas Products for Cosmetics and Pharmaceuticals," (1977).

Domino Sugar Corporation, "Co–crystallization ".
Domino Sugar Corporation, "Raspberry".
Domino Sugar Corporation, "Molasses Dark".

*Primary Examiner*—Thurman K. Page
*Assistant Examiner*—William E. Benston, Jr.
*Attorney, Agent, or Firm*—Kirk M. Miles; John F. Levis

[57] ABSTRACT

The present invention is a saccharide-based matrix, and the products resulting therefrom, made from a maltodextrin feedstock subjected to conditions which induce flash flow of the maltodextrin so that the matrix possesses a physically or chemically altered structure from the feedstock. The present invention also includes a method of producing the matrix and of making products which take advantage of the unique properties of the matrix.

46 Claims, No Drawings

5,709,876
Page 2

U.S. PATENT DOCUMENTS

| | | | |
|---|---|---|---|
| 3,981,739 | 9/1976 | Dmitrovsky et al. | 127/60 |
| 3,991,766 | 11/1976 | Schmitt et al. | 128/335.5 |
| 4,056,364 | 11/1977 | Dmitrovsky et al. | 23/273 |
| 4,072,658 | 2/1978 | Okamoto et al. | 260/49 |
| 4,086,418 | 4/1978 | Turbak et al. | 536/30 |
| 4,136,145 | 1/1979 | Fuchs et al. | 264/164 |
| 4,159,210 | 6/1979 | Chen et al. | 127/29 |
| 4,164,448 | 8/1979 | Röeschlau et al. | 435/11 |
| 4,166,005 | 8/1979 | Masurekar et al. | 436/190 |
| 4,168,205 | 9/1979 | Danninger et al. | 435/10 |
| 4,178,393 | 12/1979 | Gregersen | 426/653 |
| 4,186,251 | 1/1980 | Tarbutton | 435/11 |
| 4,194,063 | 3/1980 | Frank et al. | 435/12 |
| 4,199,373 | 4/1980 | Dwivedi et al. | 127/60 |
| 4,241,178 | 12/1980 | Esders et al. | 435/15 |
| 4,271,199 | 6/1981 | Cherukuri et al. | 426/5 |
| 4,293,292 | 10/1981 | Israel | 425/9 |
| 4,293,570 | 10/1981 | Vadasz | 426/3 |
| 4,303,684 | 12/1981 | Pitchon et al. | 426/312 |
| 4,335,232 | 6/1982 | Irwin | 528/128 |
| 4,338,350 | 7/1982 | Chen et al. | 426/658 |
| 4,348,420 | 9/1982 | Lynch et al. | 426/272 |
| 4,362,757 | 12/1982 | Chen et al. | 426/599 |
| 4,371,516 | 2/1983 | Gregory et al. | 424/22 |
| 4,376,743 | 3/1983 | Dees | 264/103 |
| 4,382,963 | 5/1983 | Klose et al. | 426/3 |
| 4,382,967 | 5/1983 | Koshida | 426/96 |
| 4,492,685 | 1/1985 | Keith et al. | 424/28 |
| 4,496,592 | 1/1985 | Kuwahara et al. | 426/5 |
| 4,500,546 | 2/1985 | Turbak et al. | 514/781 |
| 4,501,538 | 2/1985 | Bray | 425/9 |
| 4,504,508 | 3/1985 | Bell et al. | |
| 4,511,584 | 4/1985 | Percel et al. | 426/99 |
| 4,526,525 | 7/1985 | Oiso et al. | 425/9 |
| 4,581,234 | 4/1986 | Cherukuri et al. | 426/3 |
| 4,585,797 | 4/1986 | Cioca | 514/773 |
| 4,619,833 | 10/1986 | Anderson | 426/548 |
| 4,643,894 | 2/1987 | Porter | 514/778 X |
| 4,684,534 | 8/1987 | Valentine | 427/3 |
| 4,722,845 | 2/1988 | Cherukuri et al. | 426/5 |
| 4,747,881 | 5/1988 | Shaw et al. | 106/209 |
| 4,765,991 | 8/1988 | Cherukuri et al. | 426/3 |
| 4,772,477 | 9/1988 | Weiss et al. | 426/99 |
| 4,793,782 | 12/1988 | Sullivan | 425/7 |
| 4,797,288 | 1/1989 | Sharma et al. | 424/476 |
| 4,816,283 | 3/1989 | Wade et al. | 426/565 |
| 4,839,184 | 6/1989 | Cherukuri et al. | 426/307 |
| 4,846,643 | 7/1989 | Yamamoto et al. | 425/7 |
| 4,853,243 | 8/1989 | Kahn et al. | 426/564 |
| 4,855,326 | 8/1989 | Fuisz | 514/777 |
| 4,857,331 | 8/1989 | Shaw et al. | 424/439 X |
| 4,867,986 | 9/1989 | Desai et al. | 424/464 |
| 4,871,501 | 10/1989 | Sugimoto et al. | 264/211.22 |
| 4,872,821 | 10/1989 | Weiss | 425/9 |
| 4,873,085 | 10/1989 | Fuisz | 424/400 |
| 4,879,108 | 11/1989 | Yang et al. | 424/440 |
| 4,882,144 | 11/1989 | Hegasy | 424/80 |
| 4,885,281 | 12/1989 | Hanstein et al. | 514/53 |
| 4,900,563 | 2/1990 | Cherukuri et al. | 426/5 |
| 4,931,293 | 6/1990 | Cherukuri et al. | 426/5 |
| 4,933,192 | 6/1990 | Darling | 426/98 |
| 4,939,063 | 7/1990 | Tamagawa | 430/138 |
| 4,978,537 | 12/1990 | Song | 426/5 |
| 4,981,698 | 1/1991 | Cherukuri et al. | 426/5 |
| 4,988,529 | 1/1991 | Nakaya et al. | 426/569 |
| 4,997,856 | 3/1991 | Fuisz | 514/777 |
| 5,009,893 | 4/1991 | Cherukuri et al. | 424/440 |
| 5,009,900 | 4/1991 | Levine et al. | 426/96 |
| 5,011,532 | 4/1991 | Fuisz | 106/215 |
| 5,028,632 | 7/1991 | Fuisz | 514/772 |
| 5,034,421 | 7/1991 | Fuisz | 514/772 |
| 5,037,662 | 8/1991 | Poulose et al. | 426/52 |
| 5,039,446 | 8/1991 | Estell | 252/174.12 |
| 5,041,377 | 8/1991 | Becker et al. | 435/220 |
| 5,057,328 | 10/1991 | Cherukuri et al. | 426/5 |
| 5,066,218 | 11/1991 | Silver | 426/20 |
| 5,073,387 | 12/1991 | Whistler | 426/7 |
| 5,077,076 | 12/1991 | Gonsalves et al. | 426/565 |
| 5,079,027 | 1/1992 | Wong et al. | 426/633 |
| 5,082,682 | 1/1992 | Peterson | 426/564 |
| 5,082,684 | 1/1992 | Fung | 426/602 |
| 5,084,295 | 1/1992 | Whelan et al. | 426/565 |
| 5,089,606 | 2/1992 | Cole et al. | 536/54 |
| 5,094,872 | 3/1992 | Furcsik et al. | 426/578 |
| 5,096,492 | 3/1992 | Fuisz | 106/215 |
| 5,096,710 | 3/1992 | Minagawa et al. | 514/778 X |
| 5,104,674 | 4/1992 | Chen et al. | 426/573 |
| 5,110,614 | 5/1992 | Corbin et al. | 426/555 |
| 5,128,145 | 7/1992 | Edgren et al. | 424/439 X |
| 5,164,210 | 11/1992 | Campbell et al. | 426/5 |
| 5,169,657 | 12/1992 | Yatka et al. | 426/5 |
| 5,169,658 | 12/1992 | Yatka et al. | 426/5 |
| 5,171,589 | 12/1992 | Richey et al. | 426/5 |
| 5,173,317 | 12/1992 | Hartman et al. | 426/6 |
| 5,173,322 | 12/1992 | Melachouris et al. | 426/580 |
| 5,175,009 | 12/1992 | Synosky et al. | 426/3 |
| 5,196,199 | 3/1993 | Fuisz | 424/401 |
| 5,236,734 | 8/1993 | Fuisz | 426/641 |
| 5,238,696 | 8/1993 | Fuisz | 426/641 |
| 5,268,110 | 12/1993 | Fuisz | 426/565 |
| 5,275,822 | 1/1994 | Valentine et al. | 424/439 X |
| 5,279,849 | 1/1994 | Fuisz et al. | 426/658 |
| 5,284,659 | 2/1994 | Cherukuri et al. | 424/441 |
| 5,286,513 | 2/1994 | Fuisz | 426/641 |
| 5,288,508 | 2/1994 | Fuisz | 426/5 |
| 5,346,377 | 9/1994 | Bogue | 425/9 |
| 5,348,758 | 9/1994 | Fuisz et al. | 426/660 |
| 5,354,559 | 10/1994 | Morehouse | 424/439 X |
| 5,374,447 | 12/1994 | Fuisz | 426/641 |
| 5,466,461 | 11/1995 | Della Valle et al. | 514/778 X |

SACCHARIDE-BASED MATRIX

BACKGROUND OF THE INVENTION

This application is a divisional of Ser. No. 08/365,591 filed Dec. 28, 1994, now U.S. Pat. No. 5,597,608, which is a division of U.S. application Ser. No. 07/847,595 filed Mar. 5, 1992, now U.S. Pat. No. 5,387,431 which is a continuation-in-part of Ser. No. 07/782,430 filed Oct. 25, 1991, abandoned.

The present invention relates to a new saccharide-based matrix which can be used in food products, and to a method of making same, as well as methods of using the new material.

Food technology in recent years has focused on providing high quality food products which are low in calorie content and low in cost. Similarly, the pharmaceutical industry is concerned with efficient delivery systems which are relatively inexpensive and accessible. To this end, ingredients are constantly being sought for their versatility and compatibility with major food products and common medicaments, such as analgesics, antibiotics, etc.

Carbohydrates have always been a major component of the human diet. Sugars, in particular, have been used extensively as a food ingredient. Materials containing both simple sugars and polymers of saccharides have also been used as ingredients in food products and in pharmaceutical delivery systems. Food grade saccharides are available as mono-, di-, tri-, tetra-, pentasaccharides and oligomers, and as carbohydrates having a large number of monosaccharide molecules, e.g., greater than 10 monosaccharide units, which are known as polysaccharides.

Saccharide-based products can have varying degrees of low-monomer saccharides, or sugars, oligomers, and polysaccharides, such as starch. Some saccharide-based products are prepared by hydrolysis of starch and are classified by the degree of starch polymer hydrolysis. The measuring unit is referred to as D.E. or dextrose equivalent. D.E. is defined as reducing sugars expressed as dextrose and reported as a percentage of the dry substance.

A saccharide-based product having high short-carbon-chain content, e.g., glucose and low-unit oligomers thereof, usually results in a higher dextrose equivalent, (D.E.). However, saccharide-based material having greater long-carbon-chain content, e.g., high monomer unit oligomers and polymers usually results in a lower D.E. rating.

For example, maltodextrins contain a mix of sugars and polysaccharides which range from long-chain oligomers resulting from starch hydrolysis to sugars having a low number of monomeric units. Under FDA guidelines maltodextrin consists of nonsweet, nutritive saccharide polymers having a D.E. of less than 20, while corn syrup solids is regarded by the FDA as having a D.E. greater than 20. The present inventor, however, refers to maltodextrins collectively as saccharide-based material consisting of nonsweet, nutritive saccharide polymers and other oligomers having six-carbon monomer units which collectively provide a carrier material capable of forming a matrix.

Maltodextrins have been used as a nonfat additive. One of the greatest advantages of maltodextrins is that they do not act adversely on the intestinal tract. Consequently, they are particularly useful as a bulking agent and as a fat substitute. Moreover, maltodextrins are generally recognized as safe (GRAS) by the United States Food and Drug Administration.

Unfortunately, the ability to disperse maltodextrins and to use them in different products is limited by their physical and chemical cohesiveness. They are unlike their high sugar counterparts in that they are relatively unreactive and physically resistive to mixing and dispersing. While artisans have been able to process sugar to enhance its utility in food and medicaments, the maltodextrins do not appear to be as versatile.

In U.S. Pat. No. 4,855,326, issued Aug. 8, 1989, various substances having pharmacological properties were combined with sugar and spun into fibers to produce a Water-soluble product. The various examples enumerated in the patent all involved the use of water soluble medicaments and were directed to enhancing the solubility rate of the different substances. The patent describes methods for combining a medicament with any one or more of the water soluble melt spinnable sugars and spinning the combination to produce a readily soluble floss form of the medicament. The disclosure of such patent is incorporated herein by reference.

In U.S. Pat. No. 5,011,532, issued Apr. 30, 1991, oleaginous substances, such as vegetable oil, mineral oil, baby oil, margarine, lanolin, cocoa butter and the like, are disclosed as characteristically lacking affinity for water. The '532 patent explains how this characteristic is altered by mixing the oleaginous substance with sugar and melt spinning the mixture in a cotton candy spinning machine or the equivalent. As so modified the products disperse in water forming a colloidal or pseudo-colloidal dispersion. Such modification enabled such widely disparate procedures as: (a) incorporating shortening oil in a cake mix containing flour but no egg to which water is added to produce a batter; and (b) producing a confection or medicated lozenge by dehydrating the dispersion and allowing the melted residue to solidify. The disclosure of the '532 patent is incorporated herein by reference.

Other disclosures dealing with spinning substances with one or more sugars will be found in U.S. Pat. Nos. 4,873,085; 4,997,856; 5,028,632; and 5,034,421, issued, respectively, Oct. 10, 1989, Mar. 5, 1991, Jul. 2, 1991, and Jul. 23, 1991.

The above-identified disclosures are directed to melt spinning sugar by introducing the sugar to a cotton-candy spinning machine. Generally such equipment is operated at a temperature of around 200° C. at a speed of about 3500 r.p.m. Melt spin in such equipment relies on the characteristics of sucrose, such as high crystallinity and high physical and chemical lability. Thus, it has been the belief of the artisan that sucrose is an important ingredient in feedstock for melt spin processing.

In fact, attempts to spin low-sucrose-containing saccharides have been generally unsuccessful. Feedstock having low D.E. or no sucrose as a carrier component chars during melt spinning and is generally non-processible, especially on a commercial scale.

SUMMARY OF THE INVENTION

The present invention includes a saccharide-based matrix resulting from a maltodextrin feedstock which has been subjected to melt-spin conditions sufficient to induce flash flow of the feedstock so that the resulting matrix possesses physically or chemically altered structure from that of the feedstock. The maltodextrin feedstock of the present invention is a saccharide-based solid material consisting of nonsweet, nutritive saccharide polymers and other glucose-bearing oligomers as well as glucose units, which collectively provide a carrier material capable of forming a matrix. The dextrose equivalent (D.E.) of the maltodextrin feedstock is less than 40, and in a preferred embodiment, between 20 and 40. In yet another preferred embodiment, the maltodextrin has a D.E. between 10 and 20.

The carrier component provided by the feedstock has a high glucose profile. A high glucose profile means that the elements include a large amount of six-carbon mono- and disaccharides as well as other glucose-based oligomers.

Preferably, the combined amount of mono-, di-, and tri-saccharides in the feedstock is 25% or greater on a dry solid basis. In other embodiments, the combined amount of mono-, and di-saccharides in the feedstock is 15% or greater on a dry solids basis. The feedstock contains no sucrose, or sucrose in insignificant amounts with respect to the overall carbohydrate profile. It is noted that while other materials, such as sucrose and other sugars, may be incorporated in the feedstock for other purposes, the resulting method and product will still be within the present invention.

The process of the present invention includes subjecting the feedstock simultaneously to flash heating and applied physical force such that the solid material experiences sufficient internal flow to transform the feedstock to a solid matrix which has a physically and chemically altered structure from that of the feedstock. The flash heating temperature and the duration of heating, however, is below that which would cause degradation of the maltodextrin feedstock.

In the case of melt spinning, it has been found that in one embodiment of the invention, a flash heat temperature in the range of 140° C. is useful in conjunction with the centrifugal force generated by spinning a head of 5.5 inches in diameter at 3,500 r.p.m. The maltadextrin feedstock in this case had a dextrose equivalent of between 34 and 38 and a combination of glucose di- and monosaccharides of about 34 to 35 percent by weight. The carbohydrate profile of the feedstock also includes oligomers having pentasaccharide, i.e., five unit, and greater monomeric unit at level of about 40%. In many embodiments, a flash heat period of less than about five seconds has been found to be effective.

In one separate embodiment, feedstock is primarily maltooligosaccharides. Maltooligosaccharides are produced by selective hydrolysis of corn starch followed by removal of high and low molecular weight compounds. The maltooligosaccharide mixture includes oligomers having the structure,

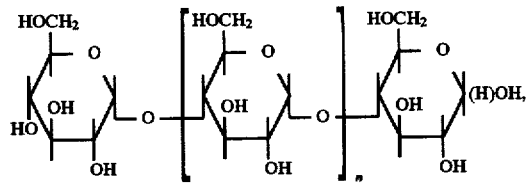

where n=1 to 8, with trace amounts of higher n. The $G_1$–$G_3$ (i.e., mona-, di-, and trimer) content of the feedstock should be at least 25% or greater on a dry solids basis. The maltooligosaccharide embodiment is particularly suitable for a high energy food product which includes peanut butter in the feedstock or in the end product or in both matrix and end product. Moreover, the resulting mattoaligosaccharide mixture, which is usually in the form of a flake, is ideally suited for inclusian of a medicament, or, alternatively, far inclusion of a flavor ingredient.

As a result of the present invention, an excellent food grade saccharide-based matrix can be provided for use in foods and in pharmaceuticals. Thus, an essentially nonsweet, low calorie inexpensive material can be used as an ingredient for bulking and dispersing in food products. Additional products such as pharmaceuticals, cosmetics and those containing most material suitable for incorporation of the new matrix are contemplated for use in the present invention.

This new matrix can be used alone or in combination with other ingredients as a means for dispersing the added ingredient throughout the material. For example, the particles, chips, flakes, spicules or combinations thereof can be used to disperse oleaginous materials which are otherwise relatively non-disperable because of the physical characteristics of such materials. In fact, oleaginous-containing matrix is useful for retaining oleaginous material with or without emulsifiers in baked goods without the need of a surfactant or other additives for holding such material in dough during preparation.

The applications for this new material are vast. Consequently, the food and pharmaceutical artisans have been equipped with a new tool which can be used to significantly enhance food products and medical delivery and industrial systems without unwanted flavor or side effects.

Moreover, the present invention can be used with dyes to provide a saccharide-based matrix with a dye incorporated therein.

For a better understanding of the present invention, references made to the following description and its scope will be pointed out in the appended claims.

DETAILED DESCRIPTION OF THE INVENTION

The present invention concerns the formation of a new solid matrix material from a maltodextrin feedstock. Maltodextrins are composed of water soluble glucose polymers obtained from the reaction of the starch with acid or enzymes in the presence of water. The hydrolysis reaction produces a carbohydrate mixture of saccharides having a dextrose equivalence (D.E.) of less than 20, or greater than 20 when the hydrolysis proceeds to produce what the FDA has termed corn syrup solids.

The maltodextrin of the present invention, however, has been selected as possessing unique properties for purposes of the present invention. Specifically, the maltodextrin feedstock of the present invention includes a carrier component which is capable of being processed from a solid through a flash flow condition to a new solid having altered physical and chemical structure. Moreover, the maltodextrins of the present invention are those mixtures resulting from hydrolysis as described above which have a D.E. of less than 40. In a preferred embodiment of the present invention the D.E. is between 20 and 40, and in yet another preferred embodiment the D.E. is between 10 and 20. Maltodextrins which are useful in the present invention include some products which are sold under the trademark MALTRIN®, a product of the Grain Processing Corporation of Muscatine, Iowa.

The inventive matrix of the present invention is prepared by subjecting solids as described above to a melt-spin process (or conditions comparable thereto) which provide sufficient internal flow to permit the transition in structure without degradation of the material. Internal flow occurs when the infrastructure of the material breaks down sufficiently to permit movement of material at a subparticle level, and probably at a molecular level. At a molecular level, internal flow contemplates the movement of molecules relative to each other.

Internal flow of material is generally associated with melting point or glass transition point. However, it is contemplated that the combined application of heat and external force is sufficient to produce the flow at temperatures below the melting or glass transition point for most compositions.

It is only when the unique combination of selected feedstock and appropriate conditions are applied thereto that the unique matrix material can be produced in accordance with the present invention. Elements outside these conditions appear to prevent or retard processability.

In fact, various experiments carried out using saccharide-based materials of varying composition demonstrated that processing maltodextrins indiscriminantly with melt spinning apparatus resulted in charring of the feedstock and non-processability of the material. The non-processability resulted in the material being only partially spun, and other deteriorative effects on the resulting matrix. In fact, when maltodextrins were combined with varying amounts of corn oil and polydextrose in varying amounts were spun, the resulting product was charred and the spinning head of the apparatus became clogged. For example, when a 23 gram sample of dried soup was mixed with 12 grams of maltodextrin and 12 grams of corn oil, the mixture would not spin through the spinning apparatus.

In further experiments, maltodextrins were intimately contacted with corn oil by processing in a food processor. When the blended material was melt spun, the resulting material was charred and brown in color. The mixture was then added to water but much of it did not readily dissolve. Furthermore, it had a burned flavor and was generally quite unacceptable for any use whatsoever. Even when lower temperatures were used in the spinning apparatus, the mixture of maltodextrins and corn oil resulted in brown woodchip-appearing material with a display of fringe floss-like material. The substance dispersed in water but appeared to be very oily and did not demonstrate any noticeable miscibility.

Other experiments were tried using maltodextrin in combination with corn oil and additives such as salt which resulted once again in charring and unsatisfactory matrix product.

Surprisingly, however, it has been found that if the feedstock is correctly tuned and subjected to correct melt-spinning conditions, a completely new matrix material can be produced which results from the alteration of the physical and chemical structure of the original feedstock. This fine tuning of the ingredients and the process parameters includes the use of a maltodextrin feedstock as defined herein which has a matrix capable of undergoing the specified transition. This feedstock is introduced to the apparatus as a solid material and the resulting matrix is also a solid material.

The apparatus is operated at a temperature and speed which permits flash flow but does not deteriorate the material undergoing the processing. Consequently, there is no resulting charring or clogging, nor is there unwanted side product having a different characteristic than that which is desired. Usually the resulting matrix product is in the form of a particle, flake, spicule, or other generally non-descript aggregate capable of subsequent processing in accordance with generally accepted techniques.

Furthermore, the feedstock material usable in the present invention is capable of being processed with additional component(s) which are incorporated in the desired product, but do not detract from its appearance or utility. Thus, the maltodextrin solids and the additive contained in the solids can be altered with respect to various characteristics including disperability, and mixability, in/or with various media. In some aspects, the products of the present invention can be used in lieu of freeze dried materials.

The nature and amount of other component or components used with the maltodextrins will vary the properties of the mixture from the standpoint of spinning. The addition of water or other liquids changes the rheology of the melt-spun material and can have an effect on the size and shape of the flakes and/or spicule-like particles.

Thus, the matrix can be used to carry oleaginous substances and permit the use of such oleaginous materials to be dispersed easily and uniformly in other materials such as foods. The oleaginous materials can be included in the melt-spun malt dextrin feedstock with numerous hydrophobic materials with which oleaginous materials would otherwise be incompatible. Moreover, a variety of hydrophobic materials can be combined in a product such as food or otherwise, and yet be able to perform their separate functions when and if they are exposed to an aqueous media.

Thus, in one aspect of the invention, ingestible food and food ingredient materials can be admixed and combined with the maltodextrin prior to melt spinning of the mixture. Ingredients suitable for admixture with the maltodextrin starting material include ready-to-use products such as soup mixes, beverage mixes, food sauces, gravy mixes, condiments, flavor compositions and components of flavor compositions, nutritional supplements, low-calorie food materials, food conditioning agents, dehydrated vegetable fluids such as orange juice and tomato juice, dehydrated animal fluids such as beef "extract," oils, fats natural and/or synthetic sweeteners, acidifying agents, alkalizing agents, food supplements, such as vitamins and/or minerals, extracts, spices, seasonings, amino acids, poly-peptides, reducing sugars to permit Maillard browning, and food grade vehicles such as propylene glycol, and the like.

Another of the important uses for the solids and corn syrup solid-based materials provided by the processes of this invention is the preparation of pharmaceutical materials.

Suitable categories of active ingredient that may be employed in the present invention may vary widely. Illustrative categories and specific examples include:

(a) Antitussives, such as dextromethorphan, dextromethorphan hydrobromide, noscapine, and chlophedianol hydrochloride;

(b) Antihistamines, such as chlorpheniramine maleate, phenindamine tartrate, doxylamine succinate, and phenyltoloxamine citrate;

(c) Decongestants, such as phenylephrine hydrochloride, phenylpropanolamine hydrochloride, pseudoephedrine, hydrochloride ephedrine;

(d) Various alkaloids, such as codeine phosphate, codeine sulfate and morphine;

(e) Mineral supplements such as potassium chloride and calcium carbonates, magnesium oxide and other alkali metal and alkaline earth metal salts;

(f) Laxative, vitamins and antacids;

(g) Ion exchange resins such as cholestyramine;

(h) Anti-cholesterolemic and anti-lipid agents;

(i) Antiarrhythmics such as N-acetyl-procainamide;

(j) Antipyretics and analgesics such as acetaminophen, aspirin and ibuprofen;

(k) Appetite suppressants such as phenylpropanolamine hydrochloride or caffeine; and (l) Expectorants such as guaifenesin.

A non-limiting list of other active ingredients includes antiinflammatory substances, coronary dilators, cerebral dialtors, penpheral vasocilators, anti-infectives, psychotropics, antimanics, stimulants, gastrointestinal agents, sedatives, anti-diarrheal preparations, anti-anginal drugs, vasodialators, anti-hypertensive drugs, vasoconstrictors and migraine treatments, antibiotics, tranquilizers, antipsychotics, antitumor drugs, anticoagulants and antithrombotic drugs, hypnotics, anti-emetics, anti-nauseants, anticonvulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropoietic drugs, antiasthmatics, cough suppressants, mucolytics, antiuricemic drugs, and mixtures thereof.

The pharmaceutical compositions contemplated herein are particularly well-suited for use when it is desired to disperse medicaments in aqueous liquids and/or to cover the undesirable tastes possessed by many pharmacologically active ingredients. Examples of such materials include acetaminophen and other bitter medicaments. Generally, the medicament is mixed with maltodextrins and a flavoring agent and/or a sweetening agent and the mixture is melt spun to obtain the pharmaceutically active product with the flavor of unpleasant medicaments masked.

In one embodiment, the present invention also includes cosmetic products, i.e., those products which include ingredients having cosmetic activity. Such products can be used for treating hair or skin cosmetically. The active ingredient can be included (1) within the matrix, (2) outside the matrix, or (3) be incorporated in the product both inside and outside the matrix. A non-limiting list of ingredients which have cosmetic activity includes mucopolysaccharide, biotin, nicotinamide compounds, sun screen, such as para-aminobenzoic acid, hair conditioner, and combinations thereof.

One class of food products according to the invention is improved soup mixes. These materials are frequently prepared from various dehydrated components which are packaged to protect them from ambient moisture and/or humidity. These mixes generally are unable to support significant quantities of oleaginous components because of the incompatibility of the oleaginous material with the dehydrated component, the difficulty of despersing oleaginous components in aqueous media, and the need to know the soup mix readily handled, so that it is a relatively free-flowing powder rather than a paste, as would be the case if it were combined with large quantities of fats or oils.

The saccharide-based matrices of the present invention overcome the prior art difficulties by making it possible to combine both a fat and/or oil component with conventional soup mix ingredients. The resulting product according to this invention is readily dispersible in hot or warm water, just as is the conventional or basic soup mix, but with the incorporation of the oleaginous component, it has a much richer flavor and an improved, full-bodied mouth feel. Thus, the organoleptic properties of the soup prepared from the compositions of this invention are greatly improved.

One type of soup mix according to the present invention comprises maltodextrins, an oleaginous component and a soup base component. The oleaginous component can be a conventional edible glyceride, fat or oil. In general, the oleaginous component is an animal fat such as tallow, lard, or hydrogenated animal and/or vegetable oils, such being solids at normal room temperature. In certain desirable embodiments of the invention, the oleaginous component is an unhydrogenated or lightly hydrogenated vegetable oil, such as corn oil, canola oil, cottonseed oil, sesame oil, grape-seed oil, sunflower seed oil, rapeseed oil peanut oil, and like oils. The soup base component can be widely varied depending upon the particular flavor and type of soup. Some soups such as split pea are relatively thick and heavy, while others such as a vegetable soup or broth are are much thiner and lighter in texture and taste. The soup base accordingly can comprise meat and meat extract components, vegetables, starches, extracts, spices, herbs, thickeners, and the like. An additional advantage of the use of maltodextrin matrix soups according to the present invention is that they have a good full rich mouth feel without the use of large quantities of oleaginous substances or thickeners.

Incorporating soup mix in the novel matrix of this invention can preclude the use of soup bases containing large pieces of material such as noodles, meat chunks, vegetable slices, and the like. The organoleptic perception to the consumer of the soup base is the same as a soup base which includes large particles. Moreover, the resulting melt-spun corn syrup solids-containing product can be used in conjunction with large solid materials to enhance the organoleptic qualities. The advantages of superior taste, richness and mouth feel can still be obtained.

In general in the preparation of soup mixes, the mixture to be melt spun contains from about 0.1 to 90 percent maltodextrin solids, from about 0.1 to 35 percent oleaginous component, from about 20 to about 70 percent of the soup base component, and from zero to about 3 percent lecithin. Preferably, the mixture contains from about 29 to 68 percent maltodextrins, from about 8 to 36 percent oleaginous component, from about 20 to 60 percent of the soup base component, and from zero to about 3 percent lechithin.

A related product prepared according to the invention is gravy and white sauce mix compositions. Generally, these are prepared in the same manner as the soup mixes, but with meat extracts, protein hydrolysates and the like in gravies. The white sauces are similarly prepared to contain flour and dairy components to give them their distinctive flavor and properties. Here again, the use of maltodextrins assists in dispersing the ingredients in aqueous mixtures and in providing a rich mouth feel.

Another product uniquely available according to the claimed invention is flaked or granular peanut butter. Peanut butter compositions according to the present invention have been made from the maltodextrin feedstock having a D.E. between 34 and 38, peanut butter, and optionally an additional oleaginous component. The solid peanut butter products are in themselves tasty. The solids also have a variety of uses in the culinary and confectionery arts. One example is the use of the peanut flakes and granules of this invention to flavor salads, and vegetables or other esculent materials. In the confectionery art, they are well adapted for use in the preparation of chocolate confections to which the products of this invention lend a strong, rich peanut flavor.

As with other products according to this invention, a homogeneous mixture of maltodextrins and peanut butter was prepared. The mixture contained an oleaginous component, for example, corn oil, to provide a richer flavor, and sweeteners such as honey, sugar, and the like. The peanut butter compositions according to the present invention contained sufficient glucose-bearing saccharide to act as a carrier. Generally, such compositions included from about 20 to about 70 percent maltodextrin feedstock having a D.E. of from about 34 to 38, from about 80 to about 30 percent peanut butter, up to about 20 percent of an oleaginous component, and from about zero to about ten percent of a sweetener. The preferred compositions includes from about 30 to about 70 percent of the maltodextrin feedstock and from about 70 to about 30 percent peanut butter. Some also included oleaginous component and/or a quantity of sweetener.

Another product according to the present invention is a ready-to-use mustard. This novel product is well-suited for use in food preparation including salads, sandwiches, and as a condiment on ham, beef, and other meat products. The mustard product has been prepared by making a mixture of maltodextrin feedstock having a D.E. of between 34 and 38, mustard base and any desired adjuvants, melt spinning the mixture so formed, and recovering the solid melt-spun product. As used herein, the mustard base includes mustard or ground mustard seed and can also include the adjuvants used in the manufacture of prepared mustard.

These mustard adjuvants include vehicles such as acetic acid, oils and spices such as tumeric, and the like. The mustard adjuvants are desirably combined with ground mustard seed, and the ingredients are combined into a homogeneous mixture. The mustard component is then combined with the maltodextrin and the combination is then melt spun. The resulting solid material recovered from the melt spinning is in effect a dry stabilized mustard product. It is readily used by combining it with meat, poultry, salad ingredients, vegetables and the like to provide a mustard flavor. It can be used in prepackaged, ready-to-eat foods or it can be used as a condiment on salad and the like as set forth herein.

A further product according to the present invention is a ready-to-use catsup. This novel product is well-suited for use in food preparation including salads, sandwiches, eggs, vegetables and as a condiment on ham, beef, and other meat products. The catsup product is prepared by making a mixture comprising maltodextrin and a tomato base or catsup, melt spinning the mixture so formed, and recovering the solid melt-spun product. As used herein, the catsup base includes tomatoes or a tomato product such as tomato paste and can also include the adjuvants used in the manufacture of prepared catsup.

These catsup adjuvants include vehicles such as water, spices such as salt, onions, garlic, natural and artificial flavors, and sweeteners such as corn syrup, sucrose, dextrose and the like. It will be understood by those skilled in the art that the adjuvants can be added in a number of forms; thus, onion powder, onion oil or a combination thereof can be used. The catsup adjuvants are desirably combined with the tomato component, and the ingredients are combined into a homogeneous mixture. The catsup component is combined with the maltodextrin feedstock and then melt spun. The resulting solid material recovered from the melt spinning is in effect a dry stabilized tomato catsup product. It is readily used by combining it with meat, poultry, salad ingredients, vegetables and the like to provide a catsup flavor. It can be used in prepackaged, ready-to-eat foods or it can be used as a condiment on salad and the like as set forth herein.

Another esculent material readily prepared according to the present invention is a mayonnaise-like product which uses much less amounts of oil than conventional products. The key to the preparation of such materials is the use of the maltodextrin matrix of the present invention with oil in melt spun form. A mixture is prepared to contain maltodextrin feedstock and vegetable oil oleaginous component. The Vegetable oil can be a natural or very lightly hydrogenated vegetable oil, such as corn, soybean, sunflower seed, cottonseed, rapeseed (canola), sesame, grapeseed or the like oil. The maltodextrin feedstock and oil is then melt spun, and the solid product is recovered. Generally, the feedstock is present in an amount greater than the oleaginous component for this embodiment of the invention. The quantity of oleaginous material should be sufficient to provide a reasonable quantity of oil in the recovered solids, but it should not be enough to cause the solids to become patently oily. In general, the oleaginous component should comprise from about ten to about 40 percent of the melt-spun material.

The mayonnaise-like product is prepared by beating egg yolks and adding the saccharide-based product resulting from the maltodextrin solids with the oleaginous component. This mixture is then flavored with salt, mustard, vinegar, citrus juice, and the like. In addition to the foregoing flavor constituents, other conventional ingestibly acceptable ingredients, including vehicles such as water and preservatives and/or antioxidants such as calcium disodium ethylene diamine tetracetic acid and butylated hydroxyanisole and the like, can be used. The result is a very appetizing mayonnaise-like food which can be used in all the instances where mayonnaise or salad dressing is used. The advantage of this product is its lower fat content.

It will be appreciated by those skilled in the art from the present description that products other than esculent products can be prepared with the maltodextrin material of the present invention. For example, a cosmetic composition can be prepared to contain an oil-soluble material such as fragrance materials, perfumes, sunscreens, topical medicaments and the like.

In another embodiment of the invention, it is possible to incorporate gelling agents such as xanthan and other gums in the saccharide-based matrix product. Examples of suitable hydrogels include materials such as xanthan gum, guar gum, carrageenan gum, gum tragacanth, alginates (e.g., sodium alginate), gum karaya, locust bean gum, gum acacia, mixtures thereof and the like. Gelling compositions have been prepared with maltodextrin feedstock having a D.E. of from about 34 to 38 and a gelling agent such as xanthan gum, melt spinning the mixture, and recovering a solid product. The quantity of gelling agent in the composition should be sufficient to provide the necessary gelling. On the other hand, the agent must be incorporated into the matrix so that it is held until ready for use. It is desirable in certain embodiments that the gelling compositions according to the invention contain from three to 40 percent, and preferably 5–20 percent, of the gelling agent with the remainder substantially being corn syrup solids.

In use, the saccharide-based gelling agent is for instance dispersed in water or an aqueous liquid. The gelling agent or gums are frequently difficult to dissolve or disperse in the liquid to be gelled. The novel melt-spun gelling compositions according to the invention, however, readily disperse.

In yet another embodiment of the invention, it is possible to incorporate emulsifiers such as those used in edible products and especially baked goods in the saccharide-based matrix product. A non-limiting list of such emulsifiers include mono and diglycerides of fats, oils and fatty acids, propylene glycol esters of fats, lactylated fatty acids, polysorbates, polyglycerol esters, ethoxylated mono and diglycerides, lecithin and the like and mixtures thereof.

It will be understood by those skilled in the art from the present description that additional adjuvants can be included with the maltodextrins and other functional ingredients. Thus, colors, dyes, pigments, antioxidants, antifungal agents, preservatives, cosmetics and such can be added to improve the appearance, aroma, shelf-life or other properties of the products prepared herein. When an esculent or pharmaceutical product is involved, it will be understood that the product contains other adjuvants which are particularly suited for the end use.

When maltodextrin feedstocks are melt spun according to the present invention, a solid material results. It is frequently in the form of flake-like particles, the size of which varies according to the material and the process conditions. Under some processing conditions, the solid product formed will vary from particulate to floss-like. With some mixtures, higher processing temperatures produce a flake-like material; with others, a particulate material is obtained at the higher temperature.

EXAMPLES

The following examples serve to provide further appreciation of the invention but are not meant in any way to restrict the effective scope of the invention.

Example 1

Samples of feedstock, e.g., two maltodextrins identified as "Maltrin" M365 (D.E.=36) and "Maltrin" M255 (D.E.=25), made by Grain Processing Corporation; Muscatine, Iowa, were prepared by reducing agglomerations of the maltodextrins to a free-flowing solid powder. Each material was introduced to a melt spinning apparatus having an open circular spinning head with a diameter of about 5.5 inches traveling at a rotational velocity of from about 3400 to about 3600 r.p.m. and melt spun at low temperature to provide white flakes.

Under these conditions the material was flung instantaneously against the inside surface of the spinning head which has been provided with a heat "ribbon." The heating ribbon was maintained at a relatively low temperature of from about 130° C. to about 180° C. for flash heating the maltodextrin feedstock. Unlike previous attempts to melt spin maltodextrins at "cotton candy" spinning conditions, a solid white matrix material was produced which possessed a physical and chemical structure different from the feedstock. A table has been set forth below which reports the conditions for producing the inventive matrix.

Example 1

| FEEDSTOCK | TEMPERATURE OF RIBBON | RPM* | PRODUCT |
|---|---|---|---|
| Sugar | 200° C. | 3600 | Fibers |
| Sugar with reducing sugar (lactose) | 210° C. | 3600 | Fibers |
| Reducing Sugar (lactose) | 224–229° C. | 3600 | Floss |
| Maltodextrin (D.E. 20) | 200° C. | 3600 | Charred Matrix unuseable |
| Maltodextrin (D.E. 34–38) | 165° C. | 3600 | White chip or flake |
| Maltodextrin (D.E. 25) | 140° C. | 3600 | White chip or flake |

*Size of spinning head is 5.5 inches; head openings are slits which are 3–5 mm long by 0.5–0.75 mm wide.

The inventive flakes and/or chips were contacted with an aqueous medium and found to dissolve in what appeared to be a true solution.

Simply stated, a non-sucrose, saccharide-based matrix possessing enhanced new physical and chemical properties resulting from flash flow alteration cannot be achieved unless the feedstock and process conditions are carefully selected in accordance with the parameters of the present invention.

In the examples that follow, unless otherwise noted, the maltodextrin was "Maltrin" M365 (D.E.=36.5). In a number of the examples the maltodextrin was Maltodextrin 35R (D.E.=35) produced by A. E. Staley Mfg. Co., of Decatur, Ill. For simplicity, the use of such material will be indicated by the following entry: "35R maltodextrin."

Example 2

A mixture of 89.9% (45.1 g) of maltodextrin D.E. 36 and 10.1% (5.1 g) of garlic oil was prepared. The garlic oil was obtained from Penta Mfg. Co., of Fairfield, N.J. This mixture was processed in accordance with the present invention to produce uniform white flakes which provided an excellent bulking mass.

The flake product itself has a sweet taste which subsequently became perceived as a very strong garlic taste. When placed in water it formed a colloid.

Example 3

A mixture was prepared by combining 38.4% (20.3 g) of sifted "Knorr" soup mix and 37.9% (20.5 g) maltodextrins D.E. 36. To the resulting mixture was added 23.7% (12.5 g) of corn oil, and the entire composition was mixed thoroughly. The mixture was then fed to the apparatus used herein.

The resulting material appeared as a substantially uniform particulate which was recovered from the spinning bowl and tested by contacting with warm water. The suspension was colloidal and excellently dispersed. The flavor system in this product was very well-rounded without organoleptic sharpness of any form. These results are attributed to the modifying effect of the oil in the product.

Example 4

A thorough mixture of 32.3% (16.4 g) of sieved "Knorr" soup mix, 31.9% (16.2 g) of maltodextrins D.E. 36, and 35.8% (18.1 g) of corn oil was prepared. The mixture was processed in accordance with the present invention to provide a particulate, spiculate product. There was also some free oil in the product.

This product was dispersed in a cup of warm water and appeared to be colloidal. The flavor was excellent. Some surface oil appeared in the product, but it was evident that this system could tolerate a heavy load of oil. Indeed, this contained over 50% more oil as the product of Example 3.

Example 5

A mixture is prepared to contain 83% (12.5 g) of maltodextrin D.E. 36 and 17% (25.5 g) of corn oil. This mixture was processed in accordance with the present invention at a speed of about 3600 r.p.m. and at a temperature of about 140°. The mixture spun at high temperature provides smaller flakes than that spun at low temperature. Both were usable as a food grade matrix material.

Example 6

A mixture was prepared to contain 16.7% (8.4 g) of acetaminophen (obtained from Sigma Chemical Co. of St. Louis, Mo.), 30% (15.0 g) of corn oil, and 53.3% (26.7 g) of maltodextrins D.E. 36. The mixture was processed in accordance with the present invention. The melt spun product was a white particulate having a slightly bitter taste.

Example 7

A mixture was prepared to contain 30% (15.1 g) of maltodextrins D.E. 36 and 70% (35.1 g) of raw peanut butter. The ingredients were mixed in a glass mortar. The mixture was then processed according to the present invention to produce a small-particulate, soft, flake-like material. The product has a dry appearance. The flavor is very good. It will be noted that this Example is made up of 30 percent maltodextrins, yet is capable of providing a product with excellent peanut butter texture and taste properties.

Example 8

A mixture was prepared with 79.6% (39.4 g) of maltodextrins D.E. 36 and 20.4% (10.1 g) of "Mazola" brand corn oil. The ingredients were mixed in a porcelain mortar. The resulting mixture was then processed at a low heat setting of 140° C. Surprisingly, the resulting solid product was in the form of small spicule-like flakes, which, when added to water, formed a colloidal dispersion.

Example 9

A mixture was prepared by beating three egg yolks for three minutes and then adding 15 g of the product of Example 8 dissolved in the juice of one lemon (ReaLemon®) plus one teaspoonful of salt and ½teaspoonful of mustard powder and two teaspoonfuls of white vinegar. Thereupon, the mixture was beat for three additional minutes. The result is a delicious mayonnaise without the use of the cup of oil called for by the recipe. The product has the appearance found to be typical of the colloidal or colloidal-like materials produced according to this invention.

It will be apparent to those skilled in the art that the present invention provides the capability of making foods with organoleptic properties providing a creamy mouth feel without the same amount of oleaginous component usually included.

Example 10

A mixture containing 20% (400 ml) of canola oil and 80% (1600 g) of 35R maltodextrin D.E. 34.5 was prepared by mixing in a food processor for 30 minutes. This blend was processed at a low temperature setting of about 140° C. Nevertheless a high quality solid chip product was recovered which could easily be used in food products as a bulking ingredient and as a dispersing agent.

Example 11

A mixture was prepared to contain 90.8% (22.8 g) of maltodextrin, 4.3% (1.1 g) of aspartame ("Nutrasweet", from Searle Inc. of Skokie, Ill.), and 4.9% (1.2 g) of corn oil. The ingredients were mixed by hand in a glass mortar. The mixture was then processed to produce a solid in the form of flakes and spicules. It was very sweet and pleasant-tasting. The product thus provides a readily usable sweetener with improved organoleptic properties, which is incorporated substantially uniformly in a bulking/dispersing agent.

Example 12

A mixture was prepared to contain 9.2% (4.6 g) of Keltrol xanthan gum (obtained from Merck & Co., Rahway, N.J., U.S.A.), 81.8% (41 g) of maltodextrins D.E. 36, and 9% (4.5 g) of Mazola corn oil. These ingredients were mixed with a glass mortar. The resulting mixture was then processed in accordance with the present invention.

The product was a high quality solid in the form of chips or flakes. A 1.1 g quantity of this product (containing about 0.1 g of the xanthan gum) is added to 25 g of warm tap water. The product quickly disperses but slowly dissolves and forms a gelatin-like material.

As a comparison, 0.1 g of the same xanthan gum is added to 25 g of water in the same manner. It disperses very slowly. It can accordingly be appreciated that the product of the present invention provides a superior way to disperse xanthan gum for food use and for industrial uses. Xanthan gum has been spun at levels up to 40% of the melt-spun mixture.

Example 13

A mixture was prepared from 50% (25 g) of tomato extender (obtained from Deltown Chemurgic of Greenwich, Conn.), 25% (12.5 g) of maltodextrins D.E. 36, and 20 25% (12/5 g) of corn oil. The mixture was processed according to the present invention to provide a granular material capable of being easily added to food products.

The flavor of the original tomato extender is extremely spicy and astringent. The processed product retains a very astringent, spicy flavor with an added sweet note. When the product is suspended in warm water, it appears to be colloidal, and the aqueous product is extremely concentrated in flavor.

Example 14

A mixture was prepared from 49.8% (12.5 g) of French's Homestyle Chicken Gravy Mix, 25.1% (6.3 g) of maltodextrins D.E. 36 and 25.1% (6.3 g) of corn oil. The mixture was processed by spinning at about 140° C. to produce a flake-like product.

Example 15

A mixture was prepared by combining 20% (10 g) black strap molasses and 80% (40 g) maltodextrins D.E. 36, the material was processed at a low temperature setting of about 140° C.

The feedstock readily spun without clogging the apparatus to provide a product in the form of dark brown chips with an excellent molasses flavor.

Example 16

A pharmaceutical was prepared to contain 10% (10 g) sucralfate (obtained from Orion Corporation, Ltd. of Espoo, Finland), 5% (5 g) xanthan gum, 5% (5 g) corn oil, and 80% (8 g) maltodextrins D.E. 36. The material was mixed with a mortar and pestle and processed in accordance with the present invention to provide a high quality particulate product.

In its original form sucralfate is a white amorphous powder practically insoluble in water. However, when 10 g of the resulting product was placed in an aqueous medium, the material dispersed and provided a suspension which possessed a pleasing mouthfeel and was substantially flavorless.

Example 17

A mixture was prepared to contain 4.948% (25 g) "Bonivita Brand" grape-seed oil, 4.948% (25 g) cocoa butter, 4.948% (25 g) herbal fragrance, 84.117% (425 g) of maltodextrins 35R D.E. 34.5 and 0.049% (0.25 g) FD&C blue dye dissolved in 0.99% (5 g) of ethanol. The resulting mixture was processed at a temperature of about 140° C. and 3600 r.p.m.

The solid feedstock underwent flash flow condition to produce a product in the form of blue flakes. About 25 g of the product, when placed in a bath full of water, produces a pleasing bath water with a nice blue color, herbal scent, and skin feel.

Example 18

A protein mixture was prepared to contain 57.9% (29 g) of maltodextrin solids D.E. 36, 29.9% (15 g) of whey proteins, and 12.2% (6.1 g) of corn oil. This mixture was processed at about 140° C. to produce a flake-like product.

This product appeared to retain its color during processing, and, when suspended in water, a resulting suspension appeared to be colloidal.

Example 19

A mixture was prepared to contain 70% (35 g) of maltodextrins D.E. 36, 25% (12.5 g) of, Casein, Acid Hydrolysate, (obtained from Sigma Chemical Co. of St. Louis, Mo.), and 5% (2.5 g) of corn oil. This mixture was processed to provide a light tan flake. When suspended in water, the flake appeared to form a colloidal dispersion.

Example 20

A mixture was prepared with 10% (5 g) corn oil, 2% (1 g) carrageenan (obtained from FMC Corporation of Philadelphia, Pa.), and 88% (44 g) of maltodextrin D.E. 36. The material was spun at a low temperature setting of about 140° C. to provide as a flake-like material. When 10 g of this material was placed in 20 g of water a thick colloidal dispersion was formed.

Example 21

A mixture was prepared to contain 25% (25 g) "Vaseline Brand" petroleum jelly from Cheseborough—Ponds Inc. of Greenwich, Conn., and 75% (975 g) of corn syrup solids. This mixture was processed at 140° C. to produce a product in the form of white flakes that formed a colloidal dispersion when placed in warm water.

Example 22

A mixture was prepared to contain 50% (25 g) of "Pillsbury" flour equilibrated at 100% relative humidity and 50% (25 g) of maltodextrins. The mixture was processed satisfactorily to produce a product somewhat dry which appears as a small "puffed" flake.

Example 23

A mixture was prepared to contain 48.9% of "Pillsbury" flour, 29.1% of maltodextrins, 9.8% of corn oil, 9.8% of water, and 2.4% of lecithin. The mixture was subjected to flash flow conditions to produce an oily granular material which disperses in water.

Example 24

A mixture was prepared to contain 58.7% of sieved "Knorr" soup mix, 29.6% of maltodextrin D.E. 34.5, 9.2% of corn oil, and 2.5% of lecithin (Thermolec 68, obtained from ADM Ross & Rowe of Decatur, Ill.). The mixture was processed according to the present invention to produce a particulate material in the form of spicules, which dispersed readily in warm water.

Example 25

A mixture was prepared to contain 5% (5 g) cyanine dye and 95% (95 g) of maltodextrins D.E. 36 were combined in a glass mortar and pestle. The mixture was processed in accordance with the present invention to produce a bright green flake that readily disperses and dissolves in water to form a bright green solution.

Example 26

A mixture was prepared to contain 20% (10 g) fluorochemical (obtained from Lehn & Fink Products Group of Montvale, N.J.), 2% (1 g) of Triton X 100 (obtained from Sigma Chemical Co. of St. Louis, Mo.), and 78% (39 g) of maltodextrins D.E.34.5.

The material was processed to produce a product in the form of flakes. When placed in water, a colloidal dispersion was formed.

Example 27

A medicament mixture was prepared to contain 10% (5 g) of Allontoin, a skin ulcer therapeutic, (obtained from Lehn & Fink Products Group) and 90% (45 g) of 35R maltodextrin D.E.34.5. The Chemical Abstracts names for Allontoin and (2,5-Dioxo-4-imidazolidinyl) urea; 5-ureidohydantoin; glyoxyldiureide; and cordianine. It is a product of purine metabolism. The material was mixed in a porcelain mortar and subject to flash flow processing in accordance with the present invention. The melt-spun product was in the form of flakes, and, when placed in water, formed a cloudy solution. A similar amount of material which had not been processed would not go into solution when placed in water.

Example 28

A confection mixture was prepared to contain 60% (30.1 g) of raw peanut butter, 10.1% (5.1 g) of honey, 29.9% (15 g) of maltodextrins D.E. 36. This mixture was processed to produce a light granular powder having a pleasant flavor. The transformation of the physical form of the feedstock was quite dramatic.

Example 29

A mixture was prepared to contain 20% (10 g) of permethyl from Lehn & Fink Products Group and 80% (40 g) of 35R maltodextrins. The mixture was blended in a glass bowl and processed at a low temperature setting of about 140° C.

Example 30

A mixture was prepared to contain 0.5% (.25 g) "Lysol" fragrance and 99.5% (50 g) of 35R maltodextrins D.E. 34.5. The mixture was blended for 3 minutes and process by subjecting it to flash flow conditions to produce a high quality white flake with a sweet, pleasant "Lysol" fragrance. When placed in water the flakes dissolved to form a weak colloid.

Example 31

A mixture was prepared to contain 20% (10 g) of amphomer from Lehn & Fink Products Group and 80% (40 g) of maltodextrins D.E. 36. The material was mixed in a porcelain mortar and then processed under flash flow con-

Example 32

A mixture was prepared to contain 10% (5 g) of sodium bromide and 90% (45 g) of 35R maltodextrins D.E. 34.5. The powders were mixed in a mortar and processed by subjecting it to flash flow conditions.

The resultant melt spun product was in the form of white flakes.

Example 33

A mixture was prepared of 20% (10 g) d'Limonene (obtained from Lehn & Fink Products Group) and 80% (40 g) of maltodextrins D.E. 36. The mixture was processed at a low temperature of about 140° C.

The resultant material was in the form of white flakes that dissolved in water to form a colloid.

Example 34

The mixture was prepared to contain 5% (2.5 g) of Dantobrom RW (obtained from Lehn & Fink Products Group), 5% (2.5 g) of corn oil, and 90% (45 g) maltodextrins D.E. 36. The ingredients were mixed using a porcelain mortar and pestle and subsequently processed under flash flow conditions. The melt spun product was in the form of white flakes.

Example 35

A bath medicament mixture was prepared of 10% (10 g) "Quaker Oats" Oatmeal, 5% (5 g) Gleason Lite mineral oil, 80% (80 g) 35R corn syrup solids D.E. 34.5, and 5% (5 g) Blue Meadow fragrance. The oatmeal was powdered by processing in a blender for about three minutes. The oil was added and mixed well in the blender. The blended material was transferred to a mortar, the fragrance and corn syrup solids were added, and the materials were worked with a pestle for about five minutes.

The mixture was then subjected to flash flow conditions at low temperature producing chips which dispersed well when added to water. The dispersal appeared collidal and the solution provided a soothing feel and pleasant fragrance.

The product provides a superior bath product with improved dispersion when added to water.

Example 36

A mixture was prepared with 10% (20 g) Gleason Lite mineral oil, 2% (4 g) "Charlie" fragrance from "REVLON", and 88% (176 g) 35R maltodextrins D.E. 34.5. The materials were mixed with a glass rod for about 10 minutes, then processed in accordance with the invention producing white chips which were set aside.

Another mixture was prepared containing 9.896% (20 g) cocoa butter, 1.979% (4 g) "Charlie" fragrance oil, 87.086% (176 g) 35R maltodextrins D.E. 34.5, 0.049% (0.1 g) MGFD plus C Blue #1, and 0.99% (2. g Ethanol 95%. The blue dye was dissolved in the ethanol to which was added all of the other ingredients with the combination being mixed well with a glass rod for about 10 minutes. This mixture was also processed according to the invention at low temperature producing blue chips.

Next, equal parts of the white and blue chips were mixed producing a beautiful blue and white chip pattern bath oil product that dissolved rapidly in tepid water producing a gorgeous blue colloidal bath water which is very comforting to the skin.

Example 37

The following mixture was prepared from 88% (44 g) 35R maltodextrins D.E. 34.5, 2% (1 g) Gelcarin GP 379, a carrageenan powder obtained from FMC Corporation, Marine Colloids Division, Philadelphia, Pa., and 10% (5 g) corn oil ("Mazola") by mixing the dry ingredients with a glass rod and then adding to the oil followed by thorough mixing with the glass rod. The mixture was then processed according to the invention at low temperature. A high quality flakey product was obtained.

The flakes were contacted with an aqueous medicament at room temperature and stirred until dispersed. A colloidal dispersion was produced.

Example 38

In this Example, 190 grams of GATORADE® lemon-lime flavored drink mix granules were combined with 90 grams of maltodextgrin 35R D.E. 34.5, a product of the ADM Co. until a uniform mixture was obtained. Thereafter, a 10 gram quantity of MAZOLA® corn oil was geometrically added to mixture using a mortar and pestle. This mixture was then spun at the medium setting, 3500 revolution per minute (RPM) to produce yellow spicules having a crisp flavor and high impact.

Example 39

In this Example, the procedure of Example 38 was repeated, except that 150 grams of maltodextrin were combined with the same amount (190 grams) of GATORADE®. This additional amount of maltodextrin caused the spun product to take the form of larger chips rather than the spicules of Example 44. In addition, it was observed that less of the as-spun product stuck to the bin ring. The flavor impact of the chips was not adversely effected by the additional amount of maltodextrin.

Example 40

| PROTEIN PRODUCT ENHANCEMENT MATRIX | |
|---|---|
| INGREDIENTS | WEIGHT % |
| Maltodextrin D.E. 36 | 50–92 |
| Oleaginous Component | 8–36 |

In the present example, the saturated fat component of a protein product has been significantly reduced by the use of a saccharide-based spun matrix. The spun matrix agent is the maltodextrin processed by flash flow in accordance with the present invention. The matrix is formed by combining a low amount of oleaginous material, such as animal fat, or replacement such as canola oil, etc., at a percentage such that it is significantly reduced when compared to the oleaginous content of a fat-bearing protein product. The material is processed by subjecting it to flash flow conditions and recovering a flake-like particulate material which can then be introduced into a protein product such as hamburger, a soy patty, or other protein material. The recovered particulate admixes more efficiently with meat and other protein media than does the oleaginous material alone.

The result is a significantly reduced saturated fat product which emulates the texture and mouth feel of a high fat content protein product. As a result of this unique combination, meat products can be processed to significantly reduce the fat content yet perserve the organoleptic qualities of the meat product, such as mouthfeel, texture and flavor. Further examples will be provided herein which show how the flavor can be added along with the oleaginous replacement matrix.

Example 41

| SPUN MATRIX IN GROUND BEEF | |
|---|---|
| INGREDIENTS | WEIGHT % |
| Maltodextrin D.E. 36 | 80 grams |
| Canola Oil | 20 grams |

In this example the spun matrix was prepared by uniformly mixing the maltodextrin with canola oil. The mixture was spun at 3600 r.p.m. at 140° C. to produce large dry flakes. The flakes were mixed with ground beef in accordance with the following table. Beef hamburger compositions set forth in the following table were pressed in a 4-inch square hamburger press to form patties. The patties were fried over a medium gas heat for 5-minutes, surface dried on a paper towel and analyzed. A three inch diameter center plug was pressed in a two-stage potato press to extract liquids to determine liquid or juiciness content.

| Hamburger Sample | Prefried | Pressed Weight of Fried 3-inch Diameter plug | Weight of Liquids from Fried 3-inch Diameter plug | Ratio of Liquids to Solids |
|---|---|---|---|---|
| Hamburger With 20% Beef Fat | 6 oz. | 2.25 oz. | 0.9 oz. | 40.0% |
| Water | ¼ oz. | | | |
| Hamburger With 15% Beef Fat | 6 oz. | 2.3 oz. | 0.8 oz. | 34.7% |
| Water | ¼ oz. | | | |
| Hamburger With 10% Beef Fat | 6 oz. | 2.4 oz. | 0.75 oz. | 31.2% |
| Water | ¼ oz. | | | |
| Hamburger With 10% Beef Fat | 5½ oz. | 2.55 oz. | 1.1 oz. | 43.1% |
| Water | ¼ oz. | | | |
| Flakes | ½ oz. | | | |
| Hamburger With 10% Beef Fat | 5¾ oz. | 2.6 oz. | 1.05 oz. | 40.4% |
| Water | ¼ oz. | | | |
| Flakes | ¼ oz. | | | |

The samples containing flakes and corresponding reduced amount of hamburger had higher weights of juice and residual pressed solids. Also, a ratio of liquids to solids in such samples is equal or higher than hamburger with 20% beef fat. The hamburgers containing flakes were about 20% thicker after frying than the fried hamburgers without flakes. Finally, the appearance, texture and mouthfeel of the low fat hamburgers with the flakes were virtually identical to that of the high fat hamburgers.

Example 42

| HAMBURGER FLAVORANT MATRIX | |
|---|---|
| INGREDIENTS | WEIGHT % |
| Maltodextrin D.E. 36 | 78.0 |
| Canola Oil | 20.0 |
| Spices- including salt, beef flavor, pepper, garlic and onion | 2.0 |
| | 100.0 |

In this example, a flavorant-containing matrix was prepared which is suitable for enhancing the flavor of hamburger. First, the spices were uniformly mixed and thereafter combined with the oil. The maltodextrins were added to the oil-spice mixture until a uniform mixture was obtained. The uniform mixture was processed at a low setting yielding a spicy, beef-flavored flake.

Example 43

| HAMBURGER FLAVORANT MATRIX | |
|---|---|
| INGREDIENTS | WEIGHT (grams) |
| Saccharide-maltodextrin 35R D.E. 34.5 | 67.0 |
| Meat Flavored Vegetable Oil | 30.0 |
| Xanthan Gum | 1.0 |
| Carrageenan | 1.0 |
| Spices- including salt, liquid smoke, flavor, pepper, garlic and onion | 1.0 |
| | 100.0 |

In this example, a process similar to that set forth in Example 42 was undertaken to provide a hamburger flavorant-containing matrix. Initially, the vegetable oil was warmed to a liquid. The spices and xanthan gum were added to the oil and a uniform mixture was obtained. Finally, the maltodextrin was added and uniformly combined with the above ingredients. The resultant mixture was processed at a low setting and a white flake having a strong beef flavor was obtained.

Example 44

| SAUSAGE FLAVORANT MATRIX | |
|---|---|
| INGREDIENTS | WEIGHT % |
| Saccharide-Maltodextrin D.E. 36 | 78.0 |
| Canola Oil | 20.0 |
| Spices- including pork flavor, fennel, salt, pepper and garlic | 2.0 |
| | 100.0 |

In this example, the procedure set forth in Example 42 is repeated, except a flavorant-containing matrix is prepared for sausage meat products instead of hamburger. The ingredients are combined and spun in the manner set forth in Example 42. The spices are uniformly combined with the oil before the saccharide is admixed. The resultant mixture is processed, and a white, pork-flavored flake is obtained.

Example 45

HAMBURGER PRODUCT

| INGREDIENTS | WEIGHT % |
|---|---|
| Ground Beef - 93% lean | 95.0 |
| Flavorant matrix obtained as a result of Example 42 | 5.0 |
| | 100.0 |

Example 46

HAMBURGER PRODUCT

| INGREDIENTS | WEIGHT % |
|---|---|
| Ground Beef - 93% lean | 97.0 |
| Flavorant matrix obtained as a result of Example 43 | 3.0 |
| | 100.0 |

In these Examples, hamburger-containing meat products were prepared. In Example 45, the flake matrix obtained as a result of Example 42 was combined with the lean ground beef until a uniform mixture was obtained. In Example 46, the matrix obtained in Example 43 was used. In each Example, the mixtures were divided and formed into hamburgers. During cooking, the matrix flakes dissolved, releasing the spices and unsaturated oil. The matrix thus provides the texture, moisture level and flavor characteristics of a much higher fat content. With Example 46, it was also observed that the hamburger product prepared with the Example 43 matrix displayed somewhat more cohesiveness and retained juiciness.

Separately, a portion of the ground beef-flavorant flake mixture in Example 45 was cooked using a microwave. It was unexpectedly found that the anti-oxidant properties of the saccharide portion of the flake enhanced the stability of the meat so that after microwaving, the resultant patty remained moist and was browned during the cooking process. The hamburger was juicy and had a pleasing taste.

Example 47

SAUSAGE PRODUCT

| INGREDIENTS | WEIGHT % |
|---|---|
| Pork | 92.0 |
| Flavorant matrix obtained as a result of Example 44 | 8.0 |
| | 100.0 |

In this example, a flavor-enhanced sausage product is prepared by combining the pork-flavored matrix with ground pork. The mixture may then be used as sausage patties or to fill sausage casings.

Example 48

TABLE 1

FLAVORANT MATRIX

| INGREDIENTS | WEIGHT GRAMS |
|---|---|
| Hydrogenated Meat-Flavored Soybean Oil (Bunge Co.) | 100.0 |
| Maltodextrins D.E. 36 | 300.0 |
| Carrageenan | 20.0 |
| Onion Powder | 50.0 |
| Black Pepper Powder | 20.0 |
| Celery Seed Powder | 10.0 |
| Garlic Powder | 1.0 |

In this Example, a flavorant matrix suitable for salisbury steak products was prepared. Initially, the hydrogenated soybean oil was heated to a liquid. Separately, the remaining ingredients were combined and thoroughly mixed. The spice-containing mixture was then slowly added to the oil while mixing. The ingredients were then processed at a low temperature to yield flakes having a savory taste and smell.

TABLE 49

SALISBURY STEAK PRODUCT

| INGREDIENTS | WEIGHT % |
|---|---|
| Flavorant Matrix as prepared above | 5.0 |
| Ground Beef 80% Lean | 95.0 |
| | 100.0 |

The flavorant matrix and ground beef were uniformly combined in the ratio set forth above and formed into a steak shape. The steak was cooked for 4 minutes on each side at a temperature of medium-high. The cooked salisbury steak product was found to have a pleasant taste and aroma.

Example 50

SOY BURGER PRODUCT

| INGREDIENTS | WEIGHT % |
|---|---|
| Soyburger mix (ADM) | 92.0 |
| Flavorant Matrix obtained as a result of Example 7 | 8.0 |
| | 100.0 |

In this Example, the flavorant matrix prepared in Example 48 was combined with a soy burger mix obtained from the ADM, (Archer Daniels Midland) Company. The flavorant matrix and soy burger mix were uniformly combined and separated into individual patties. Upon cooking, the soy burgers were found to have an excellent taste and juiciness.

Other meats and protein media, not included in a specific example herein, are also contemplated for use in the present invention. For example, horsemeat could be used as well as mutton, lamb, venison, and many others.

Examples 51 and 52

Maltooligosaccharides (MOS) have been found especially useful as spun matrix carriers. A maltooligosaccharide is generally a saccharide wherein the polymeric linkage is through the alpha bonds rather than the beta bonds and generally contain less than ten units. The MOS available from Pfanstiehl Laboratories Inc., No. 138 has a D.E. of 27 and a mono-, di-, and tri- saccharide content of 29.4% by weight. It produces large flakes which are suitable as carriers in accordance with the following examples:

Example 51

In this example a high calorie product useful as an energy source is made with the MOS spun matrix. A mixture was prepared with 75.0 grams (75%) of MOS D.E. 27, 15 Grams (15%) corn oil, and 10 grams (10%) smooth peanut butter. The combination was mixed by hand without heating.

The mixture was subjected to flash flow conditions at a low temperature about 140° C. and at a speed of about 3600 r.p.m.. The product was a high energy flake which had an attractive appearance, quite suitable for incorporation in food.

Example 52

Similarly, a mixture was prepared with 37.05 grams (74.0%) of MOS D.E. 27, 5.57 grams (11.1%) salt, and 7.48 (14.9%) corn oil by hand mixing without heat. The mixture had the appearance of a white powder. The powder was subjected to flash flow at about 140° C. and at a speed of about 3600 r.p.m..

The resulting product was in the form of chips having a variety of sizes. The chips were both white and brown, but having a texture and appearance satisfactory for ingestion.

Example 53

In order to determine the ability to deliver high energy flavor, a test was conducted by hand mixing a combination of 42.5 grams (85%) of MOS D.E. 27, 2.5 grams (5%) of corn oil, and 5 grams (10%) of beef flavor.

While unblended pockets appeared during mixing, when the mixture was subject to flash flow conditions a translucent, light brown flake matrix appeared which had a sweet, beefy flavor.

Example 54

A medicament formulation was tested by blending a combination of 28.6 grams (57.7%) of MOS D.E. 27, 7.1 grams (14.2%) of acetominophen, and 14.3 grams (28.6%) of vegetable oil.

The blend was subjected to flash flow conditions, converting a powder to high quality white chip which is readily useable in, or as a pharamceutical delivery system.

Example 55

Another test was conducted to determine whether or not a dye-bearing matrix could be provided. A 50 mg sample of Rhodamine B dye was dissolved in ethanol (1 ml solution of 95% ethanol). 50 grams of MOS D.E. 27 was added and blended by hand.

The blend was subjected to flash flow conditions by spinning at low temperature of about 140° C. at a speed of about 3600 r.p.m.. A matrix was recovered in which the dye was substantially evenly dispersed throughout. The yield was about 75%.

Example 56

A second test was conducted similar to that of Example 55, but a greater yield of about 82% resulted.

The product from each of Examples 55 and 56 was readily useable in many applications which dye dispersions are desirable.

Exmaple 57, 58 and 59

Further tests were conducted as Examples 57, 58 and 59 using the same protocol as in Examples 2, 6, and 16, respectively. The maltodextrin component was replaced with the MOS as described in Examples 51, et seq.

The results were quite favorable. In Example 57, a flake product containing garlic oil was produced which had a strong garlic flavor and which formed a colloid when placed in water. In Example 58, an acetominophen-bearing white particulate was produced which could be easily used as a pharmaceutical delivery means. Similarly, Example 59 resulted in a high quality white particulate which included sucralfate as an active ingredient.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

What is claimed is:

1. A saccharide-based matrix comprising a feedstock including maltodextrin and a component selected from the group consisting of food ingredients, pharmaceuticals, cosmetics, dyes and mixtures thereof, which has been subjected to conditions of force and temperature which induce flash flow of said feedstock without causing degradation of said feedstock whereby said matrix possesses physically or chemically altered structure from said feedstock.

2. The saccharide-based matrix of claim 1, wherein said maltodextrin has a dextrose equivalent (D.E.) of less than about 40.

3. The saccharide-based matrix of claim 2, wherein said D.E. is from about 20 to about 40.

4. The saccharide-based matrix of claim 2, wherein said D.E. ratio is from about 10 to about 20.

5. The saccharide-based matrix of claim 1, wherein said maltodextrin consists essentially of maltooligosaccharide.

6. The saccharide-based matrix of claim 1, wherein said feedstock consists essentially of maltooligosaccharide and peanut butter.

7. The saccharide-based matrix of claim 1, wherein said feedstock comprises a flavorant and maltooligosaccharide.

8. The saccharide-based matrix of claim 1, wherein said conditions which induce flash flow comprise subjecting said feedstock simultaneously to flash heating and applied physical force.

9. The saccharide-based matrix of claim 8, wherein said conditions are created by melt-spinning said maltodextrin feedstock.

10. The saccharide-based matrix of claim 9, wherein said flash heating of said feedstock is carried out at a temperature below the degradation temperature of said feedstock.

11. The saccharide-based matrix of claim 10, wherein said flash heating temperature is sufficient to permit internal flow whereby infrastructure of a solid breaks down to permit movement of material at a subparticle level.

12. The saccharide-based matrix of claim 1, wherein said feedstock comprises a combined monomer and dimer content of at least about 15% on a dry solids basis.

13. The saccharide-based matrix of claim 1, wherein said feedstock comprises a combined monomer, dimer and trimer content of at least about 25% on a dry solids basis.

14. The saccharide-based matrix of claim 8, wherein said applied physical force is centrifugal.

15. The saccharide-based matrix of claim 1, wherein said matrix is in a solid form which is selected from the group consisting of particles, chips, flakes, spicules and combinations thereof.

16. The saccharide-based matrix of claim 1, wherein said feedstock comprises at least about 90% maltodextrin.

17. The saccharide-based matrix of claim 16, wherein said feedstock comprises at least about 95% maltodextrin.

18. The saccharide-based matrix of claim 1, wherein said food ingredient is selected from the group consisting of soup mixes, beverage mixes, food sauces, gravy mixes, condiments, expressed vegetable fluids, expressed animal fluids, natural sweeteners, synthetic sweeteners, spices, seasonings, food supplements, propylene glycol and mixtures thereof.

19. An edible product comprising a saccharide-based matrix resulting from a feedstock comprising a mixture of maltodextrin and an additional edible material being subjected to conditions of force and temperature which induce flash flow of same feedstock without causing degradation of said feedstock whereby said matrix possesses physically or chemically altered structure from said feedstock.

20. The edible product of claim 19 whereby said additional edible material is selected from the group of soup mixes, beverage mixes, food sauces, gravy mixes, condiments, expressed vegetable fluids, expressed animal fluids, natural sweeteners, synthetic sweeteners, spices, seasonings, food supplements, propylene glycol, emulsifiers, protein medium and mixtures thereof.

21. A pharmaceutical product comprising a saccharide-based matrix resulting from a maltodextrin feedstock being subjected to conditions of force and temperature which induce flash flow without causing degradation of said feedstock whereby said matrix possesses physically or chemically altered structure from said feedstock.

22. The pharmaceutical product of claim 21 which further comprises a biologically active ingredient.

23. The pharmaceutical product of claim 22 wherein said active ingredient is selected from the group consisting of antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, apetite suppressants, expectorants, antiinflammatory substances, coronary dilators, cerebral dilators, penpheral vasocilators, anti-infectives, psychotropics, antimanics, stimulants, gastrointestinal agents, sedatives, antidiarrheal preparations, anti-anginal drugs, vasodialators, anti-hypertensive drugs, vasoconstrictors and migraine treatments, antibiotics, tranquilizers, antipsychotics, antitumor drugs, anticoagulants and antithrombotic drugs, hypnotics, anti-emetics, anti-nauseants, anticonvulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropaietic drugs, antiasthmatics, cough suppressants, mucolytics, anti-uricemic drugs, and mixtures thereof.

24. The pharmaceutical product of claim 21 wherein said matrix further comprises a biologically active ingredient.

25. The pharmaceutical product of claim 24 wherein said active ingredient is selected from the group consisting of antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, apetite suppressants, expectorants, antiinflammatory substances; coronary dilators, cerebral dilators, penpheral vasocilators, anti-infectives, psychotropics, antimanics, stimulants, gastrointestinal agents, sedatives, antidiarrheal preparations, anti-anginal drugs, vasodialators, anti-hypertensive drugs, vasoconstrictors and migraine treatments, antibiotics, tranquilizers, antipsychotics, antitumor drugs, anticoagulants and antithrombotic drugs, hypnotics, anti-emetics, anti-nauseants, anticonvulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropaietic drugs, antiasthmatics,-cough suppressants, mucolytics, anti-uricemic drugs, and mixtures thereof.

26. The pharmaceutical product of claim 21 which comprises a biologically active ingredient selected from the group consisting of antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, apetite suppressants, expectorants, antiinflammatory substances, coronary dilators, cerebral dilators, penpheral vasocilators, anti-infectives, psychotropics, antimanics, stimulants, gastrointestinal agents, sedatives, antidiarrheal preparations, anti-anginal drugs, vasodialators, anti-hypertensive drugs, vasoconstrictors and migraine treatments, antibiotics, tranquilizers, antipsychotics, antitumor drugs, anticoagulants and antithrombotic drugs, hypnotics, anti-emetics, anti-nauseants, anticonvulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropaietic drugs, antiasthmatics, cough suppressants, mucolytics, anti-uricemic drugs, and mixtures thereof.

27. The pharmaceutical product of claim 21, wherein said feedstock comprises maltooiigosaccharide and a biologically active ingredient.

28. A cosmetic product comprising a saccharide-based matrix resulting from a maltodextrin feedstock being subjected to conditions of force and temperature which induce flash flow without causing degradation of said feedstock whereby said matrix possesses physically or chemically altered structure from said feedstock.

29. The cosmetic product of claim 28 which further comprises a cosmetic agent.

30. The cosmetic product of claim 29, wherein said active ingredient is selected from the group consisting of mucopolysaccharide, biotin, nicotainamide compounds, sun screen, hair conditioner and combinations thereof.

31. The cosmetic product of claim 28, wherein said matrix further comprises a cosmetic agent.

32. The cosmetic product of claim 31, wherein said cosmetic agent is selected from the group consisting of mucopolysaccharide, biotin, nicotinamide compounds, sun screen, hair conditioner and combinations thereof.

33. The cosmetic product of claim 27 which comprises a cosmetic agent selected from the group consisting of mucopolysaccharide, biotin, nicotinamide compounds, sun screen, hair conditioner and combinations thereof.

34. A dye product comprising a dye and a saccharide-based matrix resulting from a maltodextrin feedstock being subjected to conditions of force and temperature which induce flash flow without causing degradation of said feedstock whereby said matrix possesses physically or chemically altered structure from said feedstock.

35. The dye product of claim 34 wherein dye is incorporated in said feedstock.

36. The dye product of claim 35 wherein additional dye is in said product.

37. A method of preparing a saccharide-based matrix comprising subjecting a feedstock including maltodextrin and a component selected from the group consisting of food ingredients, pharmaceuticals, cosmetics, dyes and mixtures thereof, to conditions of force and temperature which induce flash flow of said feedstock without causing degradation of said feedstock whereby said matrix possesses physically or chemically altered structure from said feedstock.

38. The method of claim 37, wherein said maltodextrin has a dextrose equivalent (D.E.) of less than about 40.

39. The method of claim 37, wherein said D.E. is from about 20 to about 38.

40. The method of claim 38, wherein said D.E. is from about 10 to about 20.

41. The method of claim 37, wherein said maltodextrin consists essentially of maltooligosaccharides.

42. The method of claim 38, wherein said conditions which induce flash flow comprise subjecting said feedstock simultaneously to flash heating and applied physical force.

43. The method of claim 42, wherein said conditions are created by melt-spinning said maltodextrinfeedstock.

44. A method of preparing an edible product, comprising providing a saccharide-based matrix resulting from a maltodextrin feedstock which has been subjected to conditions of force and temperature which induce flash flow of said maltodextrin and combining said matrix with an edible material to provide an edible product.

45. The method of claim 44, wherein said matrix further comprises an edible material.

46. The method of claim 45, wherein said edible material is selected from the group consisting of soup mixes, beverage mixes, food sauces, gravy mixes, condiments, expressed vegetable fluids, expressed animal fluids, natural sweeteners, synthetic sweeteners, spices, seasonings, food supplements, propylene glycol, emulsifiers and mixtures thereof.

* * * * *